United States Patent [19]

Terry et al.

[11] Patent Number: 5,587,407
[45] Date of Patent: Dec. 24, 1996

[54] BIOCIDAL POLYMERIC COATING FOR HEAT EXCHANGER COILS

[75] Inventors: Claude E. Terry, LaGrange; Douglas E. Triestman; Daniel L. Price, both of Kennesaw, all of Ga.

[73] Assignee: Interface, Inc., LaGrange, Ga.

[21] Appl. No.: 467,011

[22] Filed: Jun. 6, 1995

Related U.S. Application Data

[60] Division of Ser. No. 864,499, Apr. 7, 1992, Pat. No. 5,453,275, which is a continuation-in-part of Ser. No. 526,394, May 21, 1990, abandoned, which is a continuation-in-part of Ser. No. 242,484, Sep. 9, 1988, Pat. No. 4,957,948.

[51] Int. Cl.$^6$ .................................. C08J 3/00; C08K 3/10
[52] U.S. Cl. .................. 523/122; 427/385.5; 428/457
[58] Field of Search .................................. 424/405, 409; 523/122

[56] References Cited

U.S. PATENT DOCUMENTS

| | | |
|---|---|---|
| 2,237,424 | 12/1943 | Stoner et al. . |
| 2,756,175 | 7/1956 | Goldstein et al. . |
| 2,922,738 | 1/1960 | McDermott et al. . |
| 2,935,490 | 4/1960 | Havens et al. . |
| 2,976,186 | 3/1961 | Thompson et al. . |
| 2,997,454 | 8/1961 | Leistner et al. . |
| 3,179,676 | 4/1965 | Stern, Jr. . |
| 3,212,967 | 10/1965 | McFadden . |
| 3,266,913 | 8/1966 | Hardy . |
| 3,364,192 | 1/1968 | Leach . |
| 3,437,721 | 4/1969 | Baranauckas . |
| 3,485,204 | 10/1969 | Patterson . |
| 3,639,583 | 2/1972 | Cardarelli . |
| 3,897,491 | 7/1975 | Toy . |
| 3,979,307 | 9/1976 | Kolaian et al. . |
| 4,235,733 | 11/1980 | Watanabe et al. . |
| 4,368,776 | 1/1983 | Negita at al. . |
| 4,647,601 | 3/1987 | McIntosh . |
| 4,718,482 | 1/1988 | Iwama . |
| 5,032,310 | 7/1991 | McIntosh, Sr. . |

FOREIGN PATENT DOCUMENTS

| | | |
|---|---|---|
| 53-081577 | 8/1978 | Japan . |
| 60-217276 | 10/1985 | Japan . |
| WO86/02369 | of 0000 | WIPO . |
| WO90/02487 | 3/1990 | WIPO . |

OTHER PUBLICATIONS

ICI Speciality Chemicals Brochure entitled "ICI Biocides--VANTOCIL® IB Microbiocide" (1989).
Technical Data Sheet on Polyhexamethylene Biguanide Hydrochloride–PHMB.
Coatings Biocide Guide, Modern Coatings, Date unknown.
Information about Antimicrobial Agents, Dow Corning, date unknown.
Information about BTC–50–USP, Sep. 1986.
Material Safety Data Sheet on Vinizene antimicrobial agent, Morton Thiokol, Inc., Oct. 1986.
Material Safety Data Sheet on Roban Biocide, NALCO, date unknown.
Material Safety Data Sheet on Proxel GXL, ICI Americas, Inc., Mar. 6, 1987.
Material Safety Data Sheet on Proxel PL, ICI Americas, Inc., Feb. 6, 1986.
Material Safety Data Sheet on 2–(4–thiazolyl) Benzimidazole, Calgon, Jan. 31, 1983.

*Primary Examiner*—Thurman K. Page
*Assistant Examiner*—William E. Benston, Jr.
*Attorney, Agent, or Firm*—Cheryl K. Zalesky; Kilpatrick & Cody

[57] ABSTRACT

A biocidal protective coating for heat exchanger coils formed by applying a polymeric composition containing an organic water resistant polymer that has associated with it an effective amount of a biocidal compound to inhibit corrosion, fouling, and biocidal buildup on the coils.

24 Claims, No Drawings

BIOCIDAL POLYMERIC COATING FOR HEAT EXCHANGER COILS

This is a divisional of U.S. Ser. No. 07/864,499 filed on Apr. 7, 1992, now U.S. Pat. No. 5,453,275 which is a continuation-in-part of U.S. Ser. No. 07/526,394, filed on May 21, 1990, now abandoned which is a continuation-in-part of U.S. Ser. No. 07/242,484 filed Sep. 9, 1988, now U.S. Pat. No. 4,957,948.

BACKGROUND OF THE INVENTION

This invention relates to a coating for, and method of coating, heat exchanger coils.

Heat exchangers are typically metal coils that conduct heat from one fluid to another fluid, such as from water or Freon (chlorofluorocarbon) inside the coils to air surrounding the coils. Examples of such coils are found in air conditioners, heaters, refrigerators, and dehumidifiers. These coils are usually manufactured from a metal such as copper, iron, brass, or aluminum, or from a metal alloy that contains zinc, manganese, silicon, chromium, nickel, magnesium or carbon. Metals are the preferred materials for heat exchangers because of their high heat transfer coefficient. Aluminum heat exchangers are widely used for car air conditioners because of their light weight, and the fact that aluminum is more efficient than steel as a heat exchange material.

Although metal heat exchanger coils are preferred for their heat transmission properties, they develop at least three very damaging conditions over time with use and exposure to the environment. First, the exterior surface of metal coils corrode on exposure to moisture and other airborne chemicals. Moisture in the air condenses on cooling coils, causing a buildup of water on the surface. The moisture corrodes the coils, causing them to be etched and pitted. This reduces the strength of the coil, and shortens the useful life and efficiency of the unit. This is especially true in areas that have a high salt content in the air.

Second, heat exchanging metal coils experience "fouling," which is the accumulation of dust and other particulate matter on the surface. Fouling decreases the efficiency of heat transfer because the particulate matter lining the outer surface of the coil generally has low thermal conductivity. In addition, fouling contributes a bad odor to the surroundings.

Perhaps the most important problem associated with the use of metal heat exchanging coils is the buildup of bacterial and fungal growth on the surface of the coils, These organisms tend to accumulate and propagate on the surface because of the presence of the moisture and particulate matter. In particular, fungi such as *Aspergillus niger, Aspergillus flavus*, and *Pencillin funiculogum*, and bacteria such as *Staphylococcus aureus* (Gram positive) and *Pseudomonas aeroginosa* (Gram negative) are known to grow under these conditions. These organisms produce a foul odor in the environment and exacerbate allergy problems. In addition, the organisms have a low thermal conductivity, which decreases the efficiency of heat transfer.

Bacterial and fungal growth are an especially significant problem for automobile air conditioners and heating units. For example, when a car air conditioner is turned on, a fan forces air past the surface of the heat exchanger coils, blowing the particulate and bacterial buildup into the passenger area. Often a strong, foul, musty odor is detected. Not only is the smell unpleasant, but it is unhealthy as well. The debris and organisms cause allergic reactions such as swollen, teary eyes, runny noses, sore throats and asthma.

Likewise, in refrigerators and freezers, a fan forces air past cooling coils and into the food compartments. The cooled air carries organisms that may contaminate the food. Furthermore, when the cooling is stopped, for example, when the refrigerator is unplugged, the organisms, especially mold, proliferate.

It is clear that the three above-described problems associated with the use of metal heat exchanger coils, corrosion, fouling, and biocidal buildup, exacerbate each other. Fouling buildup occurs more rapidly when there is corrosion on the coils, and organisms proliferate at a faster rate when there is fouling particulate and moisture to feed on.

There is therefore a strong, long felt need to develop a coating for metal heat exchangers that reduces the corrosion, fouling and biocidal buildup on the exterior surface of the coils. The desired coating must be durable, efficient, and capable of being applied to coils during manufacture.

Therefore, it is an object of the present invention to provide a coating for heat exchanger coils that protects the exterior surface of the coils from corrosion caused by moisture and other chemicals.

It is another object of the present invention to provide a coating for heat exchanger coils that prevents the buildup of dust and particulate matter on the surface of the coil.

It is a further object of the present invention to provide a coating for heat exchanger coils that prevents the buildup of micro-organisms on the surface of the coil.

It is still another object of the present invention to provide a coating for heat exchanger coils that is suitable for large scale manufacturing.

It is a still further object of the present invention to provide a process to apply a biocidal protective coating to heat exchanger coils that is simple and efficient.

SUMMARY OF THE INVENTION

A biocidal protective coating for heat exchanger coils is formed by coating coils with a polymeric composition containing an organic water resistant polymer that has associated with it an effective amount of a biocidal compound.

A broad range of biocides can be used in this coating. The biocide must be compatible with the polymeric formulation while providing protection from a wide variety of microorganisms. It must also be stable and active at the temperatures of use, as well as on exposure to moisture and light.

Any polymer, copolymer, or mixture of polymers can be used in the coating that, when associated with the selected biocidal compound, provides a water resistant biocidal protective coating. In a preferred embodiment, the polymers or copolymers are prepared from alkenes, dienes, vinyl esters, acrylics, alkylacrylic or alkyl acrylates, vinyl halides, styrene, or vinylidene halides. It is preferred that at least some of the hydrogens on the polymer be replaced with fluorine atoms.

The polymeric composition can also contain nonpolymeric extenders or fillers such as clay, calcium carbonate, diatomaceous earth, alumina trihydrate, barium sulphate, talc, calcium silicate or magnesium silicate, or polymeric extenders such as polyethylene or poly(vinylacetate ethylene). In the preferred embodiment, nonpolymeric extenders are used in a range of 0 to 10.0% by weight, and polymeric extenders in a range of 0 to 50% by weight.

The polymeric composition is applied to the heat exchanger coils by any appropriate method, for example, by dipping the coils into a dispersion of the polymeric composition, spraying the polymeric composition onto the coils, or brushing the polymeric composition onto the coils. In a preferred embodiment, the coating is applied in a thickness range of 0.0381 mm to 0.3810 mm. The coils are then dried with or without heat.

The coating provides superior corrosion resistance, and minimizes fouling caused by the accumulation of dust and other particulate matter on the coil. In addition, the coating provides long-term biocidal activity against fungi and bacteria.

DETAILED DESCRIPTION OF THE INVENTION

The present invention is a biocidal protective exterior coating for, and a method for coating, heat exchanger coils. According to the present invention, the coils are coated with a polymeric composition that includes an organic water resistant polymer that has associated with it a biocidal compound compatible with the polymeric composition that provides biocidal protection for an extended period of time. The biocide can be interspersed with the desired polymer, or alternatively, can be incorporated directly into the polymer chain.

As used herein, the term biocide refers to the ability of a compound to kill or inhibit microorganisms. An effective amount of a biocide is that amount that will kill or inhibit the growth of a significant number of microorganisms.

Substrates and Coating Thicknesses

This coating can be applied to any type of metal coil, including those made from copper, iron, brass, or aluminum, or a metal alloy that contains zinc, manganese, silicon, chromium, nickel, magnesium or carbon. The coils can be coated with this biocidal polymeric composition by any appropriate method, including dipping the coil into a dispersion of the polymeric composition, spraying the materials onto the coils, or brushing the materials onto the coils. The coils can be coated to any desirable thickness, preferably 0.1524 mm to 0.381 mm. A polymeric coating should be selected that adheres to the coil surface.

Selection of Biocide

A consideration in choosing a biocide is the spectrum of organisms to be killed. For example, certain biocides are active against Gram negative but not Gram positive organisms. Others may be active against bacteria in general but not significantly active against fungi. Certain biocides are active against a broad spectrum of organisms, including Gram negative and Gram positive bacteria and fungi.

The biocidal activity of an active compound can be tested before addition to the polymeric composition with the following assay. A microorganism is plated onto trypticase soy nutrient agar, or other appropriate media. Holes (6 mm diameter, 5 mm deep) are then punched into the agar, and 0.05 ml of the test compound, or a solution of test compound, is placed into the holes. The petri-dish is examined for growth of the microorganisms after incubation for 24 hours at 30° C. The diameter of the clear area surrounding the hole containing the compound being tested is indicative of the degree of microbiocidal activity.

Further, many commercially available biocides are supplied with manufacturer's information regarding the spectrum of activity and the minimum inhibitory concentration (MIC) of the biocide. It is recommended, however, that the manufacturer's MIC not be relied on in preparing a biocidal coating for heat exchanger coils. The MIC should be confirmed independently in the polymeric composition of choice.

The MICs for biocides can vary extensively. Very toxic biocides may be effective at a concentration of as little as 0.001% by weight. Other biocides must be used in fairly large concentrations, for example, up to 10% by weight. As examples, Irgasan DP 30 is typically effective in a concentration range of 0.5–1.5% of a 2% solution; Vantocil IB is typically effective in a concentration range of 1–5% of a 20% active aqueous solution; Amical 48 is typically effective at 200–5000 ppm (0.02% to 0.5% by weight); Vinyzene IT-3000 DIDP is typically effective in a range of 0.2 to 1.5% of a 20% active material in DOP, and Sylguard (Aegis) is typically effective in a range of 0.1 to 1.5% by weight. These ranges, of course, can vary depending on the material that the biocide is placed in and the desired application and performance level of the biocide.

In addition, a biocide must be chosen that is stable at the temperature of use. Typically this will not be a substantial concern when the composition is applied to a cooling coil, because most commercially available biocides are chemically stable at lower temperatures. It should, however, be confirmed that the low temperature has no adverse effect on efficacy.

The stability of the biocide is a greater concern when the coil is used to transfer additional heat. The polymeric composition should be tested at the operational temperature of the systems to determine the effect on stability and efficacy.

The polymeric composition that is used should not detrimentally effect the biocidal properties of the active compound, and should not unfavorably chemically react with it. Certain polymers and other components are also capable of tying up active compounds without covalently reacting with them, reducing the compound's effectiveness. As an example, a widely used biocidal compound, Sylgard, manufactured by Dow Corning Corporation, is inactivated in the presence of anionic surfactants and Triton X-100, a nonionic detergent. Its activity may also be lessened in the presence of certain polymers. The efficacy of the desired biocidal agent in a given polymeric mixture can be determined by one of ordinary skill in the art, for example, by following the procedure of Example 10.

Nonlimiting examples of biocidal compounds that may be suitable in various polymeric compositions include:

10,10-Oxybisphenarsine (OBPA, sold as Vinyzene BP-505, DOP antimicrobial agent by Morton Thiokol, Inc.);

Sylguard, (3-(trimethoxysilyl)propyloctadecyldimethyl ammonium chloride, marketed by Dow Corning Corporation);

tri-n-butyltin;

Kathon LX and Kathon CG/ICP (both containing 5-chloro-2-methyl-4-isothiazolin-3-one and 2-methyl-4-isothiazolin-3-one), manufactured by Rohm and Haas Specialty Chemicals, Inc.;

Roban 3999 Biocide (combination of metronidazole, dimethylformamide, and isopropanol), manufactured by Nalco Chemical Company;

Tektamer 38 A.D. (1,2-dibromo-2,4-dicyanobutane), manufactured by Calgon Corporation;

Proxel P1 and Proxel GXL (1,2-benzothiazolin-3-one), manufactured by ICI Americas, Inc.;

Fundex TF (tributyltin fluoride) and Fundex TO (tributyltin oxide), both manufactured by Aceto Chemical Co., Inc., 126-02 Northern Blvd., Flushing, N.Y. 11368;

Busan 11-M1 (modified barium metaborate), Busan 52 (potassium N-hydroxymethyl-N-methyldithiocarbamate, sodium 2-mercaptobenzothiazole), Busan 74 (thiocyanomethylthio benzothiazole, hydroxypropyl methanethiolsulfonate); all manufactured by Buckman Laboratories, Inc., 1256 North McLean Blvd., Memphis, Tenn. 38108;

Cosan P (N-trichloromethyl thiophthalimide); Cosan PCMC (parachlorometacresol), Cosan PMA-30 (phenyl mercury acetate solubilized), Cosan PMA-100 (Bulk) (phenylmercury acetate), Cosan PMA-100-WSB (phenyl mercury acetate in water-soluble bags), Cosan PMO-30 (phenyl mercury oleate), Cosan S (3,5-dimethyltetrahydro 1, 3, 5, 2H-thiadiazine 2-thione), Cosan 158 (complexed alkyl amine with an organotin salt), Cosan 171-S (phenyl mercury 2-ethylhexylmaleate), Cosan 265 (1,1'-(2-butenylene)-bis-(3,5,7-triaza-1-azoniaadamantane chloride)), Cosan 340 (organotin/organomercurial), and Cosan 635-W (complexed alkyl amine); all manufactured by Cosan Chemical Corp., 481 River Road, Clifton, N.Y. 07014;

Dowicide A Antimicrobial Agent (O-phenylphenol, sodium salt, tetrahydrate), Dowicide EC-7 Antimicrobial Agent (pentachlorophenol), Dowicide G Antimicrobial Agent (sodium pentachlorophenate), Dowicil A-40 Antimicrobial Agent (2,3,5-trichloro-4-propylsulfonyl pyridine), Dowicil S13 Antimicrobial Agent (2,3,5,6-tetrachloro-4-(methyl sulfonyl)pyridine), Dowicil S-13A Antimicrobial Agent (2,3,5,6-tetrachloro-4-(methyl sulfonyl)pyridine), Dowicil 75 Antimicrobial Agent (1-(3-chloroallyl)-3,5,7-triaza-1-azonia-adamantane chloride), all manufactured by Dow Chemical U.S.A., 2040 Dow Center, Midland, Mich. 48640;

Giv-Gard BNS 25%-AF (bromonitrostyrene), and Giv-Gard DXN (dimethoxane), both manufactured by Givaudan Corp., 100 Delawanne Ave., Clifton, N.J. 07014;

Dantoin DMDMH-55 (dimethylol dimethyl hydantoin) manufactured by Glyco Chemicals, Inc., 51 Weaver St., Greenwich, Conn. 06830;

Sanibond 200-LG (tetradecyl dimethylbenzyl ammonium chloride dihydrate), manufactured by Hilton-Davis Chemical Co., 2235 Langdon Farm Rd., Cincinnati, Ohio 45237;

CB-111 (copper borate), manufactured by Humphrey Chemical Corp., P.O. Box 2, Edgewood Arsenal, Md. 21010;

Intercide ATO (tributyltin oxide), Intercide FC (tributyltin oxide complex), Intercide N-628 (trialkyl organotin), Intercide PMA 18 (phenyl mercury acetate liquid), Intercide PMO 11 (phenyl mercury oleate liquid), Intercide TMP ((n-trichloromethyl)thio phthalimide), Intercide T-O (trialkyl tin compound), Intercide 60 (phenyl mercury acetate powder), Intercide 340-A (trialkyl tin compound), all manufactured by Interstab Chemicals, Inc., 500 Jersey Ave., New Brunswick, N.J. 08903;

Merbac-35 (benzyl bromoacetate), Metasol D3T (tetrahydro-3,5-dimethyl-2H-1,3,5-thiadiazine-2-thione), both manufactured by Merck & Co., Inc., Merck Chemical Division, 126 E. Lincoln Ave., Rahway, N.J. 07065;

Penta (pentachlorophenol), manufactured by Monsanto Industrial Chemical Co., 800 N. Lindbergh Blvd., St. Louis, Mo. 63166;

Omacide-645 (zinc pyridinethione-N-oxide and a polybrominated salicylanilide), and Omadine solution (40% sodium) (40% solution of sodium pyridinethione-N-oxide), both manufactured by Olin Chemicals, 120 Long Ridge Rd., Stamford, Conn. 06904;

Diaphene (3,4,5-tribromosalicylanilide), and Salicylanilide (salicylanilide), both manufactured by Pfister Chemical Works, Inc., Linden Ave., Ridgefield, N.J. 07657;

Skane M-8 (2-n-octyl-4-isothiazolin-3-one), manufactured by Rohm and Haas Co., Independence Mall West, Philadelphia, Pa. 19105;

Nuodex PMA-18 (phenyl mercury acetate), Nuosept 95 (complex organic), PMA-18 (phenyl mercury acetate), and Super Ad-It (di(phenyl mercury)dodecenyl succinate), all manufactured by Tenneco Chemicals, Inc., Intermediates Division, P.O. Box 2, Piscataway, N.J. 08854;

Troysan CMP Acetate (chlormethoxypropyl/mercury compound); Troysan PMA-10SEP (phenyl mercury compound); Troysan PM-20SEP (phenyl mercury compound); Troysan PMA-30 (phenyl mercury compound); Troysan PMA-100 (phenyl mercury compound); Troysan PMO-30 (phenyl mercury compound); Troysan 142 (heterocyclic sulfur compound); Troysan 174 (aminoethanol compound); Troysan 192 (amino propanol compound); Troysan 269 (alkyl tin compound); all manufactured by Troy Chemical Corp., One Avenue L, Newark, N.J. 07105:

Vancide TH (triazine type), manufactured by R. T. Vanderbilt Co., Inc., 30 Winfield St., Norwalk, Conn. 06855;

Glazed Penta (pentachlorophenol), manufactured by Vulcan Materials Co., Chemicals Div., P.O. Box 545, Wichita, Kans. 67201;

Irgasan DP 30 (2,4,4'-trichloro-2'-hydroxydiphenyl ether), Vantocil IB (poly(iminoimidocarbonyl iminoimidocarbonyl iminohexamethylene hydrochloride), Amical 48 (diiodomethyl p-tolyl sulfone), Vinyzene IT-3000 DIDP (2-N-octyl-4-isothiazolin-3-one);

and Keycide X-10 (stabilized form of tributyltin oxide), manufactured by Witco Chemical Corp., Organics Division, 277 Park Ave., New York, N.J. 10017.

Selection of Polymer

Any polymer, copolymer, or mixture of polymers can be used that, when associated with a biocidal compound, provides a water resistant biocidal protective coating. To achieve desired properties, other nonpolymerized compounds can also be used in the composition, for example, halogenated monomers. The polymeric composition can also include a surfactant to improve the properties of the composition. The polymer is preferably the product of a free radical polymerization, however, other types of polymers can also be used.

Nonlimiting examples of suitable monomers that can be polymerized or copolymerized to form suitable polymers include alkenes, dienes, vinyl esters, vinyl ethers, acrylic acid, acrolein, alkyl acrylic acids, including methacrylic acid, alkyl or aryl acrylate, alkyl or aryl alkylacrylic acids, including methyl methacrylate, acrylonitrile, vinyl halides, styrene, or vinylidene halide, and more specifically, ethylene, propylene, butene, 2-methyl-2-propene, pentene, 3-methyl-1-butene, 1,3-butadiene, 1,3-pentadiene, 2-methyl-1,3-butadiene, 2,3-dimethyl-1,3-butadiene, chloroprene, vinyl acetate, vinyl propionate, vinyl butyrate, methoxyethylene, ethoxyethylene, propoxyethylene, acrylic acid, acrylonitrile, methyl methacrylate, ethyl methacrylate, propyl methacrylate, butyl methacrylate, isobutyl methacrylate, vinyl chloride, polytetrafluoroethylene, polychlorotrifluoroethylene, vinyl bromide, vinyl fluoride, vinylidene chloride, vinylidene bromide and vinylidene fluoride. It is preferred that at least some of the hydrogens of these monomers be replaced with halogens, preferably fluorine, to increase the corrosion resistant properties of the coating. Chlorine or bromine can also be used. Polymers can be partially halogenated or perhalogenated.

Fluoropolymers and fluorinated monomers can typically withstand exposure to a wide variety of chemical environments and some are useful at temperatures ranging from −200° C. to as high as 260° C. Most fluoropolymers are totally insoluble in organic solvents and some are unaffected by strong acids or bases. In addition, they will not support combustion.

An example of a suitable polymeric material for use in this invention is Teflon® NPA Soil and Stain Repellent, which is a proprietary composition of fluorochemicals and nonfluorochemicals made by E. I. DuPont NeMours and Co., comprising polyfunctional perfluoroalkyl esters and perfluoroalkylmethacrylate copolymers.

Perfluorinated polymers can be used alone or in association with nonfluorinated polymers. Alternatively, different perfluorinated polymers can be used together. Nonfluorinated polymers can also be used together or in association with fluorinated polymers. Furthermore, perfluorinated monomers can be polymerized with nonfluorinated monomers to produce a suitable polymer for use in the heat exchange coating.

Compatibility of the the biocide and the polymeric composition must be considered when mixing the two materials. For example, a basic biocidal compound will cause precipitation, or coagulation, when mixed with an acidic polymeric composition. As an illustration, Troysan 174 manufactured by Troy Chemical Company is incompatible with acidic compositions, such as Teflon® NPA Soil and Stain Repellant marketed by E.I. DuPont Nemours and Company. However, Troysan 174 can be used with neutral or basic polymeric compositions. Likewise, an acidic biocidal compound should be used with an acidic or neutral polymeric composition.

Nonpolymeric and Polymeric Extenders

The polymers can be mixed with nonpolymeric "extenders" or "fillers", for example, clay, $CaCO_3$, diatomaceous earth, alumina trihydrate, barium sulphate, talc, calcium silicate, and magnesium silicate. A preferred range of nonpolymeric fillers is from 0.5% to 10.0% by weight. Fluorinated polymers can be "extended" with nonhalogenated, less expensive polymers such as polyethylene and poly(vinylacetate ethylene). In the preferred embodiment, these polymeric extenders are used in a concentration of 0 to 50%.

As described in copending application U.S. Ser. No. 07/190,370, filed May 5, 1988, by Robert McIntosh, entitled "Biocidal Delivery System and Method of Preparation Thereof," now U.S. Pat. No. 4,908,209, carrier materials such as diatomaceous earth or other high-surface area particulate inert materials actually extend the period of time during which the biocidal material is active against organisms. The biocidal material is adsorbed onto the material, and is slowly released over time. Other materials that can be used include cationic synthetic resins and natural polymers, for instance, chitin, gelatin, and collagen, having quaternary amine sites or free amine functions, and polymeric microcapsules.

The polymeric coating can be applied by any appropriate method, including dipping, brushing or spraying the coils. The coils are then dried with or without heat.

Without further elaboration, it is believed that one skilled in the art can, using the preceeding description, utilize the present invention to the fullest extent. The following specific embodiments, are, therefore, to be construed as merely illustrative, and not limiting of the remainder of the disclosure. Percentage of composition is by weight unless otherwise indicated. For ease of illustration in the following examples, Sylguard and OBPA are used as the biocidal agents. However, as described above, a very wide range of biocides can be used in the polymeric composition.

EXAMPLE 1

Biocidal Teflon Coating with Sylguard

A biocidal protective coating for heat exchangers is prepared by mixing a ratio of 99% fluoropolymer dispersion, such as Teflon® NPA soil and stain repellent, that contains 0 to 5% polyfunctional perfluoro alkyl ester and 1 to 10% perfluoroalkylmethylacrylate copolymers, and 1% active Sylguard.

EXAMPLE 2

Biocidal Teflon Coating with Irgasan DP 30

A biocidal protective coating for heat exchangers is prepared by mixing a ratio of 99% fluoropolymer dispersion, such as Teflon® NPA soil and stain repellent, that contains 0 to 5% polyfunctional perfluoro alkyl ester and 1 to 10% perfluoroalkylmethylacrylate copolymers, and 1% of a 2% solution of Irgasan DP 30.

EXAMPLE 3

Biocidal Teflon Coating with Vantocil IB

A biocidal protective coating for heat exchangers is prepared by mixing a ratio of 97% fluoropolymer dispersion, such as Teflon® NPA soil and stain repellent, that contains 0 to 5% polyfunctional perfluoro alkyl ester and 1 to 10% perfluoroalkylmethylacrylate copolymers, and 3% of a 20% solution of Vantocil IB.

EXAMPLE 4

Biocidal Teflon Coating with Amical 48

A biocidal protective coating for heat exchangers is prepared by mixing a ratio of 98% fluoropolymer dispersion, such as Teflon® NPA soil and stain repellent, that contains 0 to 5% polyfunctional perfluoro alkyl ester and 1 to 10% perfluoroalkylmethylacrylate copolymers, and 2% of a 25% aqueous solution of Amical 48.

EXAMPLE 5

Biocidal Teflon Coating with Vinyzene IT-3000 DIDP

A biocidal protective coating for heat exchangers is prepared by mixing a ratio of 98.5% fluoropolymer dispersion, such as Teflon® NPA soil and stain repellent, that contains 0 to 5% polyfunctional perfluoro alkyl ester and 1 to 10% perfluoroalkylmethylacrylate copolymers, and 1.5% of a solution of 20% active Vinyzene IT-3000 DIDP.

EXAMPLE 6

Biocidal Teflon Polyethylene Coating

A biocidal protective coating for heat exchanger coils is prepared with a composition of 48.5% aqueous Teflon® NPA soil and stain repellent fluorochemical dispersion, 47.5% polyethylene emulsion, 1% of a 5% solution of OPBA, and 2.5% ethoxylated nonylphenol (surfactant). The surfactant is first mixed with OBPA, and this mixture added to the Teflon® dispersion. The polyethylene emulsion is then added to the Teflon® mixture. This composition is then ready for use as a coating.

EXAMPLE 7

Biocidal Teflon Poly(Vinylacetate Ethylene) Coating

A biocidal protective coating for heat exchanger coils can be prepared from 47.5% Teflon® NPA soil and stain repellent aqueous fluorochemical dispersion, 47.5% ethylene vinyl acetate emulsion, 2% of a 5% solution of OBPA, and 2.5% ethoxylated nonylphenol.

EXAMPLE 8

Application of Coating by Dipping

Coils are dipped into a dispersion containing a perfluorinated polymer, 0.2 to 10% biocide, and then heated at a temperature range from 50° C. to 150° C. until dry. The coils are coated with the polymeric composition to a thickness of from 0.038 mm to 0.38 mm.

EXAMPLE 9

Application of Coating by Dipping

Coils are dipped into a dispersion containing 99% fluorinated polymeric composition and 1% of a 5% solution of OBPA, and then dried at 180° F. for ten minutes.

EXAMPLE 10

Application of Coating by Spraying

Coils are sprayed with a dispersion containing 98% fluorinated polymeric composition and 2% Sylguard, and dried at 180° F. for ten minutes.

EXAMPLE 11

Application of Coating by Brushing

Coils are brushed with a dispersion containing 98.5% fluorinated polymeric composition and 1.5% Sylguard, and dried at 180° F. for ten minutes.

EXAMPLE 12

Effectiveness of Coating to Reduce Corrosion

A coil coated in accordance with Example 9 is dried and the coils run in the cooling mode for 700 hours (approximately equal to three years of actual use of an automobile air conditioner), along with a non-treated coil. After 700 hours, the coated coils show no signs of corrosion due to exposure to water or other airborne chemicals.

EXAMPLE 13

Effectiveness of Coating to Reduce Pitting

A coil prepared in accordance with Example 9, along with an uncoated coil, is subjected to a fine mist of salt spray (sodium chloride) for 21 days and a visual comparison made. The coil coated with Teflon® NPA soil and stain repellent and OBPA shows no significant sign of corrosion due to pitting from salty water, and accumulates less particulate matter than the uncoated coil.

EXAMPLE 14

Effectiveness of Coating to Reduce Microbial Growth

The effectiveness of a biocidal compound on incorporation into a polymeric composition can be determined by the following method. A polymeric composition with biocide added is painted onto 2" by 2" by ¼" aluminum blocks and dried for twenty four hours.

A spectrophotometer is used to determine a standard optical density of bacteria solution as a function of concentration of bacteria. The innoculating culture is then diluted to a concentration of $10^4$ cells/mi. Agar seeded with bacteria is poured over the test samples to form a thin top coating. After cooling, the samples are placed in a 20° C. incubator for 18 hours. The samples are then transferred to a 37° C. incubator for an additional 18 hours. The evaluation of microbial growth can be performed using a stereomicroscope. The sample should be scanned closely and compared to a non-treated control.

EXAMPLE 15

Biocidal Effectiveness of Various Polymeric Coatings

Four sets of coils were prepared separately with 98% polyacrylate and 2% of an alkyl phosphoric acid biocide as described in Example 2 of U.S. Pat. No. 4,957,948; 98% polyethylene and 2% of partially neutralized phosphoric acid from Example 2; 97.5% polyvinyl acetate and 2.5% of the partially neutralized alkyl phosphoric acid from Example 2; and 95% Teflon® NPA soil and stain repellent with 5% of the® partially neutralized alkyl phosphoric acid from Example 2 of U.S. Pat. No. 4,957,948. These coils were inoculated with *Aspergillis niger, Aspergillis flavus* and *Penicillin funiculogum*. An uncoated coil was likewise innoculated. These coils were run in the cooling mode continuously for 21 days, and then visually observed for fungal growth. As seen in Table I, the uncoated coil showed a heavy growth of fungi after 14 days. The polyacrylate and polyethylene coatings showed only little growth of fungi after 21 days, while the polyvinylacetate showed only moderate growth of fungi after 21 days. Superior resistance to fungal growth was shown by the fluorocarbon in combination with 5% of the partially neutralized alkyl phosphoric acid, in that there was no fungal growth after 21 days.

TABLE I

Resistance to Fungal Growth

| Type Coating | Percentage Partially Neutralized Alkyl Phosphoric Acid from Example 2 | 7 Days | 14 Days | 21 Days |
| --- | --- | --- | --- | --- |
| None | 0 | 3 | 3–4 | 4 |
| Acrylate | 2 | 1 | 2 | 2 |
| Polyethylene | 2 | 1–2 | 1–2 | 1–2 |
| Polyvinylacetate | 2.5 | 2 | 3 | 3 |
| Teflon ® | 5 | 0 | 0 | 0 |

0 = No Growth (Excellent Resistance)
1 = Trace of Growth (Very Good Resistance)
2 = Little Growth (Good Resistance)
3 = Moderate Growth (Poor Resistance)
4 = Heavy Growth (No Resistance)

This invention has been described with reference to its preferred embodiments. Variations and modifications of the coating for, and method of coating heat exchanging metal coils will be obvious to those skilled in the art from the foregoing detailed description of the invention. It is intended that all these variations and modifications be included within the scope of the appended claims.

We claim:

1. A heat exchanger, comprising an exterior coating comprising:
   (a) a water resistant organic polymeric material comprising a halogenated polymer, and wherein the material bonds to the surface of the heat exchanger; and
   (b) an effective amount of 2-N-octyl-4-isothiazolin-3-one sufficient to inhibit growth of microorganisms on the heat exchanger.

2. The heat exchanger of claim 1 wherein the polymeric material comprises a polymer or copolymer prepared from monomers comprising a diene, vinyl ester, vinyl ether, acrylic acid, acrolein, alkyl acrylic acid, alkyl or aryl acrylate, alkyl or aryl alkylacrylic acid, acrylonitrile, vinyl halides, styrene, or vinylidene halide.

3. The heat exchanger of claim 1 wherein the polymeric material comprises a polymer or copolymer prepared from an alkene.

4. The heat exchanger of claim 1 wherein the polymeric material comprises a perfluorinated or partially fluorinated polymer or copolymer.

5. The heat exchanger of claim 1 wherein the polymeric material comprises a perfluoroalkyl ester.

6. The heat exchanger of claim 1 wherein the polymeric material comprises a perfluoroalkyl methacrylate polymer or copolymer.

7. The heat exchanger of claim 1 wherein the polymeric material includes a polymeric extender.

8. The heat exchanger of claim 1 wherein the biocide is incorporated into the polymer.

9. The heat exchanger of claim 1 that contains a nonionic surfactant in the coating.

10. The heat exchanger of claim 1 further comprising a nonpolymeric extender in the coating.

11. The heat exchanger of claim 10 wherein the nonpolymeric extender is selected from the group consisting of clay, calcium carbonate, diatomaceous earth, alumina trihydrate, barium sulphate, talc, calcium silicate, and magnesium silicate.

12. The heat exchanger of claim 10 wherein the nonpolymeric extender is added in a range of 0.5% to 10.0% by weight.

13. A method of protecting a heat exchanger coil comprising coating the coil with a polymeric composition comprising a water resistant organic polymeric material comprising a halogenated polymer, and wherein the material bonds to the surface of the heat exchanger; and an effective amount of 2-N-octyl-4-isothiazolin-3-one sufficient to inhibit growth of microorganisms on the heat exchanger.

14. The method of claim 13 wherein the polymeric material comprises a polymer or copolymer prepared from monomers comprising a diene, vinyl ester, vinyl ether, acrylic acid, acrolein, alkyl acrylic acid, alkyl or aryl acrylate, alkyl or aryl alkylacrylic acid, acrylonitrile, vinyl halides, styrene, or vinylidene halide.

15. The method of claim 13 wherein the polymeric material comprises a polymer or copolymer prepared from an alkene.

16. The method of claim 13 wherein the polymeric material comprises a perfluorinated or partially fluorinated polymer or copolymer.

17. The method of claim 13 wherein the polymeric material comprises a perfluoroalkyl ester.

18. The method of claim 13 wherein the polymeric material comprises a perfluoroalkyl methacrylate polymer or copolymer.

19. The method of claim 13 wherein the polymeric material includes a polymeric extender.

20. The method of claim 13 wherein the biocide is incorporated into the polymer.

21. The method of claim 13 that contains a non-ionic surfactant in the coating.

22. The method of claim 13 further comprising a nonpolymeric extender in the coating.

23. The method of claim 22 wherein the nonpolymeric extender is selected from the group consisting of clay, calcium carbonate, diatomaceous earth, alumina trihydrate, barium sulphate, talc, calcium silicate, and magnesium silicate.

24. The method of claim 22 wherein the nonpolymeric extender is added in a range of 0.5% to 10.0% by weight.

\* \* \* \* \*

UNITED STATES PATENT AND TRADEMARK OFFICE
CERTIFICATE OF CORRECTION

PATENT NO. : 5,587,407
DATED : December 24, 1996
INVENTOR(S) : Claude E. Terry et al.

It is certified that error appears in the above-indentified patent and that said Letters Patent is hereby corrected as shown below:

Column 11, line 32, claim 1(b) delete "2-N-octyl-4 -isothiazolin-3-one" and insert --poly(iminoimidocarbonyl) iminoimidocarbonyl iminohexamethylene hydrochloride--

Column 12, line 19, claim 13 delete "2-N-octyl-4 -isothiazolin-3-one" and insert --poly(iminoimidocarbonyl) iminoimidocarbonyl iminohexamethylene hydrochloride--

Signed and Sealed this

Eleventh Day of May, 1999

*Attest:*

Q. TODD DICKINSON

*Attesting Officer*    *Acting Commissioner of Patents and Trademarks*